(12) United States Patent
Kutchinsky et al.

(10) Patent No.: US 9,581,562 B2
(45) Date of Patent: Feb. 28, 2017

(54) HANDHELD DEVICE FOR ELECTROPHYSIOLOGICAL ANALYSIS

(75) Inventors: Jonatan Kutchinsky, Ballerup (DK); Nicholas Byrne, Antioch, CA (US); Christopher Mathes, Annandale, NJ (US); Jens Henneke, Hvalsø (DK)

(73) Assignee: SOPHION BIOSCIENCE A/S, Ballerup (DK)

( * ) Notice: Subject to any disclaimer, the term of this patent is extended or adjusted under 35 U.S.C. 154(b) by 705 days.

(21) Appl. No.: 14/002,671

(22) PCT Filed: Feb. 29, 2012

(86) PCT No.: PCT/EP2012/053458
§ 371 (c)(1),
(2), (4) Date: Aug. 30, 2013

(87) PCT Pub. No.: WO2012/117029
PCT Pub. Date: Sep. 7, 2012

(65) Prior Publication Data
US 2013/0334062 A1  Dec. 19, 2013

Related U.S. Application Data

(60) Provisional application No. 61/447,823, filed on Mar. 1, 2011.

(30) Foreign Application Priority Data

May 31, 2011 (EP) .................................. 111682241

(51) Int. Cl.
G01N 27/28 (2006.01)
B01L 3/02 (2006.01)
(Continued)

(52) U.S. Cl.
CPC ............ *G01N 27/28* (2013.01); *B01L 3/0275* (2013.01); *G01N 33/48728* (2013.01);
(Continued)

(58) Field of Classification Search
CPC . G01N 27/28; G01N 33/48728; B01L 3/0275; B01L 3/021; B01L 2200/0647; B01L 2200/146; B01L 2200/027; B01L 2200/0487; C12M 1/3407
See application file for complete search history.

(56) References Cited

U.S. PATENT DOCUMENTS 5,187,096 A  2/1993 Giaever et al.
6,932,893 B2  8/2005 Bech et al.
(Continued)

FOREIGN PATENT DOCUMENTS

DE  10 2006 052 231 A1  5/2008
JP  06138068 A  5/1994
(Continued)

OTHER PUBLICATIONS

Hamill et al, "Improved Patch-Clamp Techniques for High-Resolution Current Recordings from Cells and Cell-Free Membrane Patches," Pflügers Arch.—European Journal of Physiology, 1981, pp. 85-100, vol. 391.
(Continued)

*Primary Examiner* — Susan D Leong
(74) *Attorney, Agent, or Firm* — Muncy, Geissler, Olds & Lowe, P.C.

(57) ABSTRACT

A handheld device for analysis of electrophysiological properties of a cellular membrane ion channel in an ion channel containing lipid cellular membrane includes a handheld body with a pump, an electronic controller, and a disposable pipette tip including a pathway for fluid. The pathway connects an open end of the pipette tip to an analysis substrate in the pipette tip. The substrate is adapted to transmit an electrical current through the ion channel. The handheld body and the disposable pipette tip are configured to releasably attach the pipette tip to the body, to provide a hydraulic connection between the pump and the pathway, and to provide an electric connection between the electronic controller and at least one of the electrodes of the substrate. The electronic controller of the handheld body is configured (Continued)

to operate the assembled device for microfluidic analysis of aspirated fluid.

17 Claims, 15 Drawing Sheets

(51) Int. Cl.
  *G01N 33/483* (2006.01)
  *G01N 33/487* (2006.01)
(52) U.S. Cl.
  CPC ....... *B01L 3/021* (2013.01); *B01L 2200/0647* (2013.01); *B01L 2200/146* (2013.01); *B01L 2300/027* (2013.01); *B01L 2400/0487* (2013.01)

(56) References Cited

U.S. PATENT DOCUMENTS

2007/0186923 A1* 8/2007 Poutiatine ............. A61J 7/0038
          128/200.14
2007/0232984 A1 10/2007 Lovell et al.
2010/0041093 A1 2/2010 Hering

FOREIGN PATENT DOCUMENTS

| JP | 3014998 U | 8/1995 |
| JP | 2003526768 A | 9/2003 |
| WO | WO 98/54294 A1 | 12/1998 |
| WO | WO 99/31503 A1 | 6/1999 |
| WO | WO 99/47905 | 9/1999 |
| WO | WO 99/66329 A1 | 12/1999 |
| WO | WO 02/33066 A1 | 4/2002 |
| WO | WO 03/048786 A2 | 6/2003 |
| WO | WO 03/089564 A1 | 10/2003 |
| WO | WO 2012/004296 A1 | 1/2012 |
| WO | WO 2012/004297 A1 | 1/2012 |

OTHER PUBLICATIONS

Neher et al, "The Extracellular Patch Clamp: A Method for Resolving Currents through Individual Open Channels in Biological Membranes," Pflügers Arch.—European Journal of Physiology, 1978, pp. 219-228, vol. 375.

* cited by examiner

HANDHELD DEVICE FOR ELECTROPHYSIOLOGICAL ANALYSIS

TECHNICAL FIELD

The present invention relates to a handheld system for analysis of electrophysiological properties of ion channels of ion channel-containing membranes, typically lipid membrane-containing structures such as cells. Also, the invention relates to a substrate and a method for establishing an electrophysiological measuring configuration in which one or more cell membranes form a high resistive seal in a configuration with measuring electrodes, making it possible to determine and monitor a current flow through the cell membrane.

BACKGROUND OF THE INVENTION

The general idea of electrically isolating a patch of membrane and studying the ion channels in that patch under voltage-clamp conditions was outlined by Neher, Sakmann, and Steinbach in "The Extracellular Patch Clamp, A Method For Resolving Currents Through Individual Open Channels In Biological Membranes", Pflueger Arch. 375; 219-278, 1978. The authors found that, by pressing a pipette containing acetylcholine (ACh) against the surface of a muscle cell membrane, they could see discrete jumps in electrical current that were attributable to the opening and closing of ACh-activated ion channels. However, they were limited in their work by the fact that the resistance of the seal between the glass of the pipette and the membrane (10-50 MΩ) was very small relative to the resistance of the channel (10 GΩ). The electrical noise resulting from such a seal is inversely related to the resistance and was large enough to obscure the currents flowing through ion channels, the conductance of which is smaller than that of the ACh channel. It also prohibited the clamping of the voltage in the pipette to values different from that of the bath due to the large currents through the seal that would result.

It was then discovered that by fire polishing the glass pipettes and by applying suction to the interior of the pipette a seal of very high resistance (1-100 GΩ) could be obtained with the surface of the cell. This giga-seal reduced the noise by an order of magnitude to levels at which most channels of biological interest can be studied and greatly extended the voltage range over which these studies could be made. This improved seal has been termed a "giga-seal", and the pipette has been termed a "patch pipette". A more detailed description of the giga-seal may be found in O. P. Hamill, A. Marty, E. Neher, B. Sakmann & F. J. Sigworth: Improved patch-clamp techniques for high resolution current recordings from cells and cell-free membrane patches. Pflugers Arch. 391, 85-100, 1981. For their work in developing the patch clamp technique, Neher and Sakmann were awarded the 1991 Nobel Prize in Physiology and Medicine.

Ion channels are transmembrane proteins which catalyse transport of inorganic ions across cell membranes. The ion channels participate in processes as diverse as generating and timing action potentials, synaptic transmission, secretion of hormones, and contraction of muscles. Many drugs exert their specific effects via modulation of ion channels. Examples are antiepileptic compounds like phenytoin and lamotrigine which block voltage-dependent $Na^+$-channels in the brain, antihypertensive drugs like nifedipine and diltiazem which block voltage dependent $Ca^{2+}$-channels in smooth muscle cells, and stimulators of insulin release like glibenclamide and tolbutamide which block an ATP-regulated $K^+$-channel in the pancreas. In addition to chemically induced modulation of ion-channel activity, the patch clamp technique has enabled scientists to perform manipulations with voltage dependent channels. These techniques include adjusting the polarity of the electrode in the patch pipette and altering the saline composition to moderate the free ion levels in the bath solution.

The patch clamp technique represents a major development in biology and medicine, since this technique allows measurement of ion flow through single ion channel proteins, and also allows the study of the single ion channel responses to drugs. Briefly, in standard patch clamp technique, a thin (approx. 0.5-2μ in diameter) glass pipette is used. The tip of this patch pipette is pressed against the surface of the cell membrane. The pipette tip seals tightly to the cell and isolates a few ion channel proteins in a tiny patch of membrane. The activity of these channels can be measured individually (single channel recording) or, alternatively, the patch can be ruptured, allowing measurements of the channel activity of the entire cell membrane (whole-cell configuration). High-conductance access to the cell interior for performing whole-cell measurements can be obtained by rupturing the membrane by applying negative pressure in the pipette.

During both single channel recording and whole-cell recording, the activity of individual channel subtypes can be characterised by imposing a "voltage clamp" across the membrane. In the voltage clamp technique the membrane current is recorded at a constant membrane potential. Or—to be more precise—the amplifier supplies exactly the current which is necessary to keep the membrane potential at a level determined by the experimenter. Hence, currents resulting from opening and closing of ion channels are not allowed to recharge the membrane.

A major limitation determining the throughput of the patch clamp technique is localisation and clamping of cells and pipette, and the nature of the fluidics system, which leads the dissolved compound to cells and patches. In conventional patch clamp setups, cells are placed in experimental chambers, which may be continuously perfused with a physiological salt solution. The establishment of the cell-pipette connection in these chambers is time consuming and troublesome. Compounds are applied by changing the inlet to a valve connected to a small number of feeding bottles. The required volumes of the solution and the amount of compound to be tested are high (i.e., several hundreds of milliliters).

High throughput systems for performing patch clamp measurements have been proposed, which typically consist of a substrate with a plurality of sites adapted to hold cells in a measuring configuration where the electrical properties of the cell membrane can be determined.

U.S. Pat. No. 5,187,096, Rensselaer, discloses an apparatus for monitoring cell-substrate impedance of cells. Cells are cultured directly on the electrodes, which are then covered with a plurality of cells; thus, measurements on individual cells cannot be performed.

WO 98/54294 discloses a substrate with wells containing electrode arrays. The substrate with wells and electrodes are formed in silicon using CVD (Chemical Vapor Deposition) and etching techniques and comprises Silicon Nitride "passivation" layers surrounding the electrodes. Cells are cultivated directly on the electrode array. The substrate is adapted to measure electrophysiological properties and discloses a variety of proposed measuring schemes.

WO 99/66329, Cenes, discloses a substrate with perforations arranged in wells and electrodes provided on each side of the substrate. The substrate is formed by perforating a silicon substrate with a laser and may be coated with anti-adhesive material on the surface. The substrate is adapted to establish giga-seals with the cells by positioning the cells on the perforations using suction creating a liquid flow through the perforations, providing the anti-adhesion layer surrounding the perforations, or by guiding the cells electrically. The cells can be permeabilised by EM fields or chemical methods in order to provide a whole-cell-measuring configuration. All perforations, and hence all measurable cells, in a well share one working electrode and one reference electrode.

WO 99/31503, Vogel et al., discloses a measuring device with a passage arranged in a well on a substrate (carrier) and separating two compartments. The measuring device comprises two electrodes positioned on either side of the passage and adapted to position a cell at the passage opening. The substrate may have hydrophobic and hydrophilic regions in order to guide the positioning of the cells at the passage opening.

U.S. Pat. No. 6,932,893 (US'893) relates to a high throughput system for determining and/or monitoring electrophysiological properties of ion channels of ion channel-containing membranes, typically lipid membrane-containing structures such as cells. The system provides means for performing an automated process including preparation of the cells, preparation of the measuring configuration, and performing the measurements on a large number of cells independently. Also, the US'893 invention relates to a substrate and a method for establishing an electrophysiological measuring configuration in which a cell membrane forms a high resistive seal in a configuration with measuring electrodes, making it possible to determine and monitor a current flow through the cell membrane. More particularly, the invention relates to such a substrate, which provides means for automatically positioning cells at measuring sites using electroosmotic flow. Also, the invention relates to a main electric circuit for performing testing and measurements on cells at a plurality of sites in parallel.

SUMMARY OF THE INVENTION

Embodiments of the present invention improve on the art by offering the advantages of a handheld system for determining electrophysiological measurements. Unlike other patch clamp systems, which require external connection to a patch clamp amplifier, a digitizer and computer running patch clamp software, embodiments of the Applicants' system is self-contained. Further, embodiments of Applicants' invention is unique in that it brings the patch clamped cell to the solutions of interest (i.e. the test compounds). Conversely, other automated or semi-automated patch clamp systems require moving solutions to the patch clamped cell(s) in a fixed position. Moreover, embodiments of said handheld system will be more affordable than the larger floor model patch clamp devices and, thus, more available to universities and smaller companies.

In a first aspect, the present invention provides a handheld device for analysis of electrophysiological properties of a cellular membrane ion channel in an ion channel containing lipid cellular membrane, the device comprising:
  a handheld body comprising a housing including a pump and an electronic controller;
  a disposable pipette tip comprising a pathway for fluid, said pathway connecting an open end of the pipette tip to an analysis substrate comprised in the pipette tip, the substrate being adapted to transmit an electrical current through the ion channel in said ion channel-containing lipid cellular membrane, when said lipid cellular membrane is held at a predetermined site of the substrate; the handheld body and the disposable pipette tip being configured to releasably attach the pipette tip to the body with the open end of the pipette tip being exposed to an exterior environment, to provide a hydraulic connection between the pump of the handheld body and said pathway, and to provide an electric connection between the electronic controller and at least one electrode of the substrate, the electronic controller of the handheld body being configured to:
  operate the pump to aspirate one or more fluids including said ion channel containing lipid cellular membrane into the fluid pathway and substrate of the pipette tip;
  determine the electrophysiological properties of the cellular membrane ion channel, while the ion channel containing lipid cellular membrane makes contact with at least one of said electrodes of the substrate, and to simultaneously record current from one of said electrodes; and
  output data representative of the recorded current.

The invention also provides a disposable pipette tip for the above handheld device according to the invention, comprising a pathway for fluid, said pathway connecting an open end of the pipette tip to an analysis substrate adapted to transmit an electrical current through the ion channel in said ion channel-containing lipid cellular membrane, when said lipid cellular membrane is held at a predetermined site of the substrate; the disposable pipette tip being configured to be releasably attached to the body of said handheld device, with the open end of the pipette tip being exposed to an exterior environment, and to provide a hydraulic connection between the pump of the handheld body and said pathway, and to provide an electric connection between the electronic controller and at least one electrode of the substrate.

The invention further provides a method for analysis of electrophysiological properties of a cellular membrane ion channel in an ion channel containing lipid cellular membrane, the method comprising the steps of:
  providing a handheld body, the body comprising a housing including a pump and an electronic controller;
  providing a disposable pipette tip separate from the body, the pipette tip comprising a pathway for fluid, said pathway connecting an open end of the pipette tip to an analysis substrate adapted to transmit an electrical current through the ion channel in said ion channel-containing lipid cellular membrane, when said lipid cellular membrane is held at a predetermined site of the substrate;
  releasably attaching the pipette tip to the body with the open end of the pipette tip being exposed to an exterior environment, the pump of the handheld body hydraulically connected to said pathway, and the electronic controller electrically connected to at least one of said electrodes of the substrate;
  operating the pump to aspirate one or more fluids including said ion channel containing lipid cellular membrane into the fluid pathway and substrate of the pipette tip;
  determining the electrophysiological properties of the cellular membrane ion channel, while the ion channel containing lipid cellular membrane makes contact with at least one of said electrodes of the substrate, and while the electronic controller records current from one of said electrodes; and causing the controller to output data representative of the recorded current.

As used herein, the term substrate may designate a patch clamp electrode unit.

The at least one electrode preferably comprises electrodes for contacting test solutions, more preferably measurement and/or reference electrodes of, e.g., a patch clamp electrode unit.

The pipette tip may comprise a laminate structure comprising a plurality of layers, such as e.g. one, two, three, four, five or more layers.

One of the layers may comprise the at least one electrode. For example, electrodes for contacting internal and external test solutions may be comprised in one layer.

Another one of said layers may comprise at least one flow channel for at least one fluid. For example, channels may be provided in one layer to facilitate the movement of an external test solution, e.g. on the top surface of another layer and into a waste reservoir.

Another one of said layers may comprise at least one flow channel for at least one fluid. For example, at least one flow channel may be provided to facilitate the movement of an internal or external test solution on the bottom surface of another layer and into a waste reservoir.

One of said layers may comprise a printed circuit board.

One of said layers may comprise a gasket between other ones of the layers.

In an independent aspect, the invention also relates to a handheld device for the determination and/or monitoring of the electrophysiological properties of cellular membrane ion channels, in ion channel containing lipid cellular membranes, comprising: a handheld body (herein also referred to as a pipette body) configured to fasten a disposable pipette tip for aspirating 1 or more fluids, further provided that one of said fluids is a population of cells having said ion channel containing lipid cellular membranes, wherein further, said disposable pipette tip comprises a substrate for separating one or more fluids.

In a further independent aspect, the present invention also relates to a handheld device for the determination and/or monitoring of the electrophysiological properties of cellular membrane ion channels, in ion channel containing lipid cellular membranes, comprising: a handheld body (herein also referred to as a pipette body) configured to fasten a disposable pipette tip for aspirating 1 or more fluids, further provided that one of said fluids is a population of cells having said ion channel containing lipid cellular membranes, wherein further, said disposable pipette tip comprises a substrate having at least 2 pathways for separating said 1 or more fluids.

In a further independent aspect, the invention relates to a handheld device for the determination and/or monitoring of the electrophysiological properties of cellular membrane ion channels, in ion channel containing lipid cellular membranes, comprising: a handheld body (herein also referred to as a pipette body) configured to fasten a disposable pipette tip for aspirating 1 or more fluids, further provided that one of said fluids is a population of cells having said ion channel containing lipid cellular membranes, wherein further, said disposable pipette tip comprises a substrate having at least 2 pathways for separating said 1 or more fluids, wherein further, said substrate comprises one or more sites for holding said ion channel-containing lipid cellular membranes, one or more working electrodes, and one or more reference electrodes positioned so as for each site to be in electrical contact with at least one reference electrode, each site being adapted to hold said ion channel-containing lipid cellular membrane so as for an electrical current drawn between the working electrode of a site and a reference electrode will be transmitted by said ion channels in said ion channel-containing lipid cellular membrane.

In a further independent aspect, the present invention relates to a handheld device for the determination and/or monitoring of the electrophysiological properties of cellular membrane ion channels, in ion channel containing lipid cellular membranes, comprising: a handheld body (herein also referred to as a pipette body) configured to fasten a disposable pipette tip for aspirating one or more fluids, further provided that one of said fluids is a population of cells having said ion channel containing lipid cellular membranes, wherein further, said disposable pipette tip is comprised of 1 or more layers, further provided that at least one of said 1 or more layers comprises 1 or more electrodes capable of making an electrical connection between said 1 or more fluids.

In a further independent aspect, the present invention also relates to a handheld device for the determination and/or monitoring of the electrophysiological properties of cellular membrane ion channels, in ion channel containing lipid cellular membranes, comprising: a handheld body (herein also referred to as a pipette body) configured to fasten a disposable pipette tip for aspirating one or more fluids, wherein at least one of said fluid includes a population of cells having said ion channel containing lipid cellular membranes, wherein further, said disposable pipette tip comprises five contiguous layers, (a), (b), (c), (d), and (e); wherein:

a first one of said layers (a) comprises a printed circuit board comprising electrodes for contacting internal and external test solutions;

a second one of said layers (b) comprises a gasket;

a third one of said layers (c) comprises an external solution layer comprising channels to facilitate the movement of said external test solution on the top surface of said printed circuit board and into a waste reservoir;

a fourth one of said layers (d) comprises an internal solution layer comprising channels to facilitate the movement of said external test solution on the bottom surface of said printed circuit board and into a waste reservoir; wherein further a valve is present in said layer (d) to isolate said internal test solution; wherein said layers (c) and (d) are separated by a septum(e).

BRIEF DESCRIPTION OF THE DRAWINGS

Embodiments of the invention will now be described with reference to the accompanying drawings, in which.

DESCRIPTION OF EMBODIMENTS OF THE INVENTION

Herein, the expression "external test solution" refers to "extracellular physiological solution", external meaning outside the cell.

The expression "internal test solution" refers to "intracellular physiological solution", internal meaning inside the cell or the solution intended to provide electrical and fluidic contact with the inside of the cell.

External test solutions and internal test solutions are also referred to, herein, as fluids.

The term "substrate" as used here in refers to the surface that bonds or comes into close mechanical contact to form seals of high electrical resistance to the lipid membrane containing ion channels. Said surface is where the cells are held in place so the electrophysiological measurements can be performed. As used herein, the term substrate may designate a patch clamp electrode unit.

The substrate may comprise, consist of or be included in a chip assembly according to WO 2012/004296 or WO 2012/004297, the respective disclosures of which are hereby incorporated by reference.

As used herein, the term "microfluidics channels" refers to channels through which the internal and external solutions are moved. Cells/solutions will be moved through said microfluidic channels in the pipette tip under pneumatic control. The term "canal" is synonymous with the term microfluidic channel.

In the present application, any ion transfer channels containing a lipid membrane, such as one or more cells or an artificial membrane can be read.

Electrophysiological properties can be e.g. current flow through an ion channel, electric potential across an ion channel, or capacitance or impedance of an ion channel containing membrane. Moreover, it is possible to add individual test compounds (typically pharmacological drugs) at the or at each membrane holding location. In case more than one membrane is being analyzed at a time, individual experiments can be carried out on each membrane. An experiment can be to measure the response of the ion channels (current) to the adding of test compound.

Figure 1:
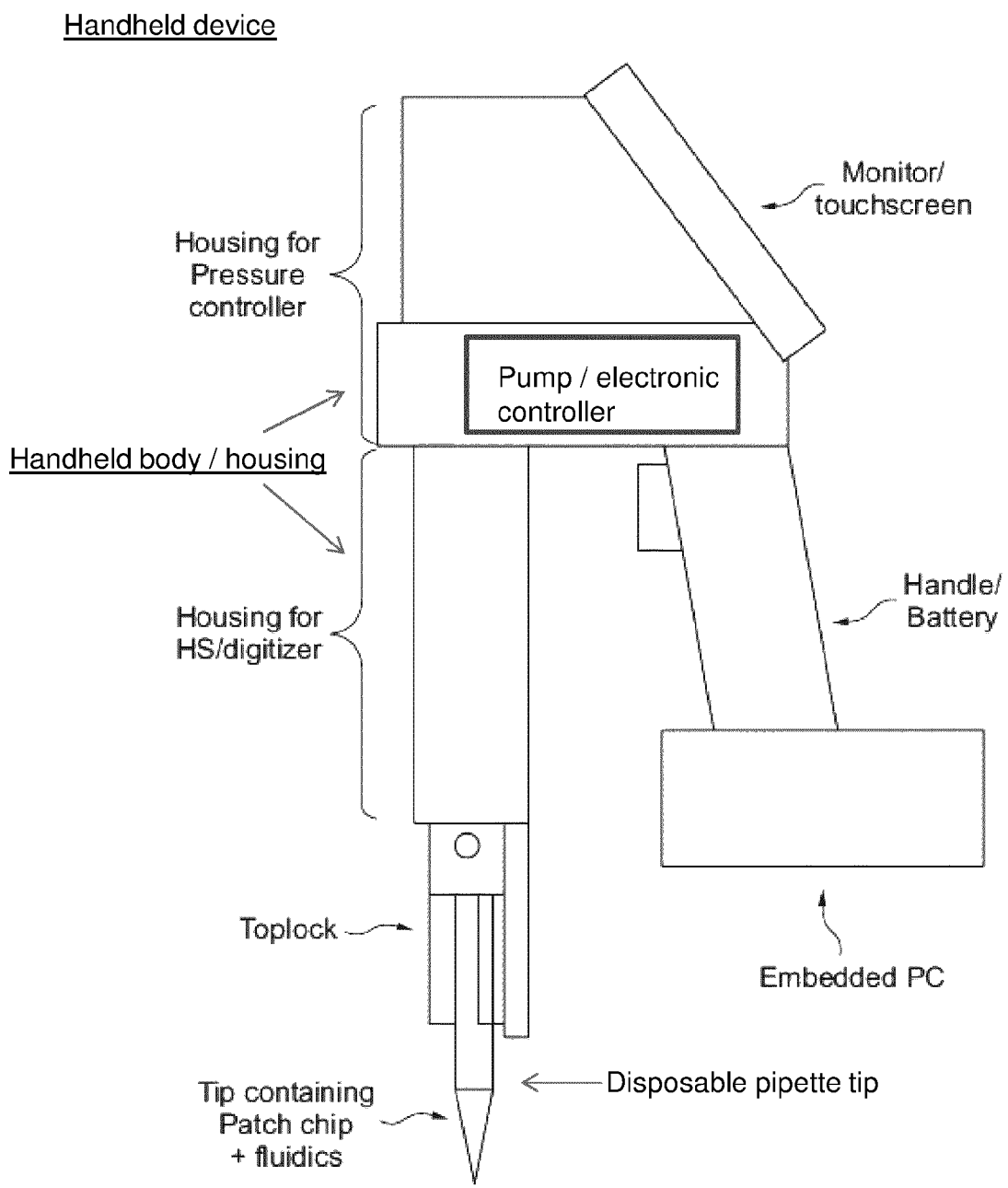
FIG. 1 is an overall schematic of an embodiment of the present invention.
Figure 2:
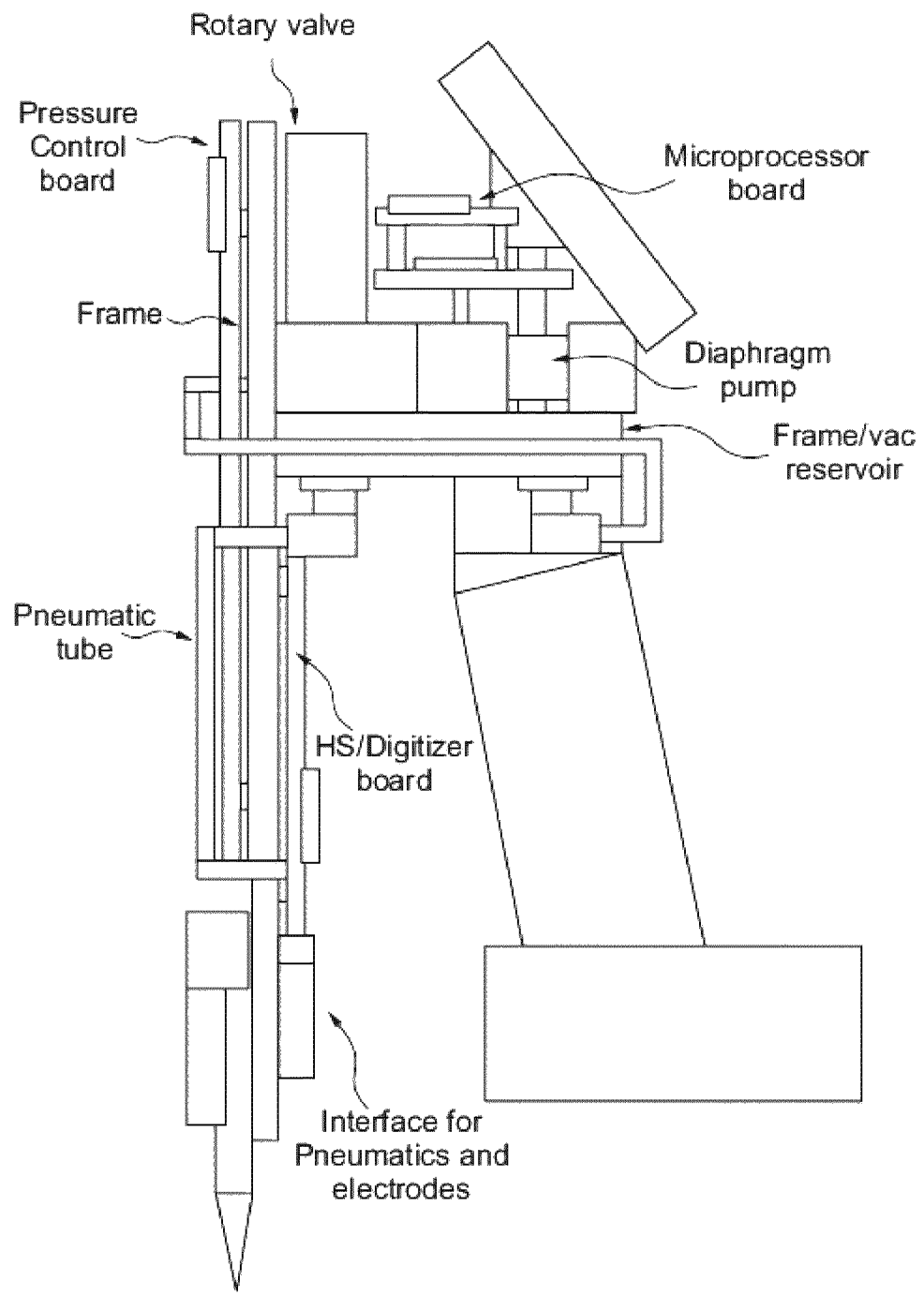
FIG. 2 is a schematic of an embodiment of the interior of the handheld body of the handheld device of the present invention.
Figure 3:
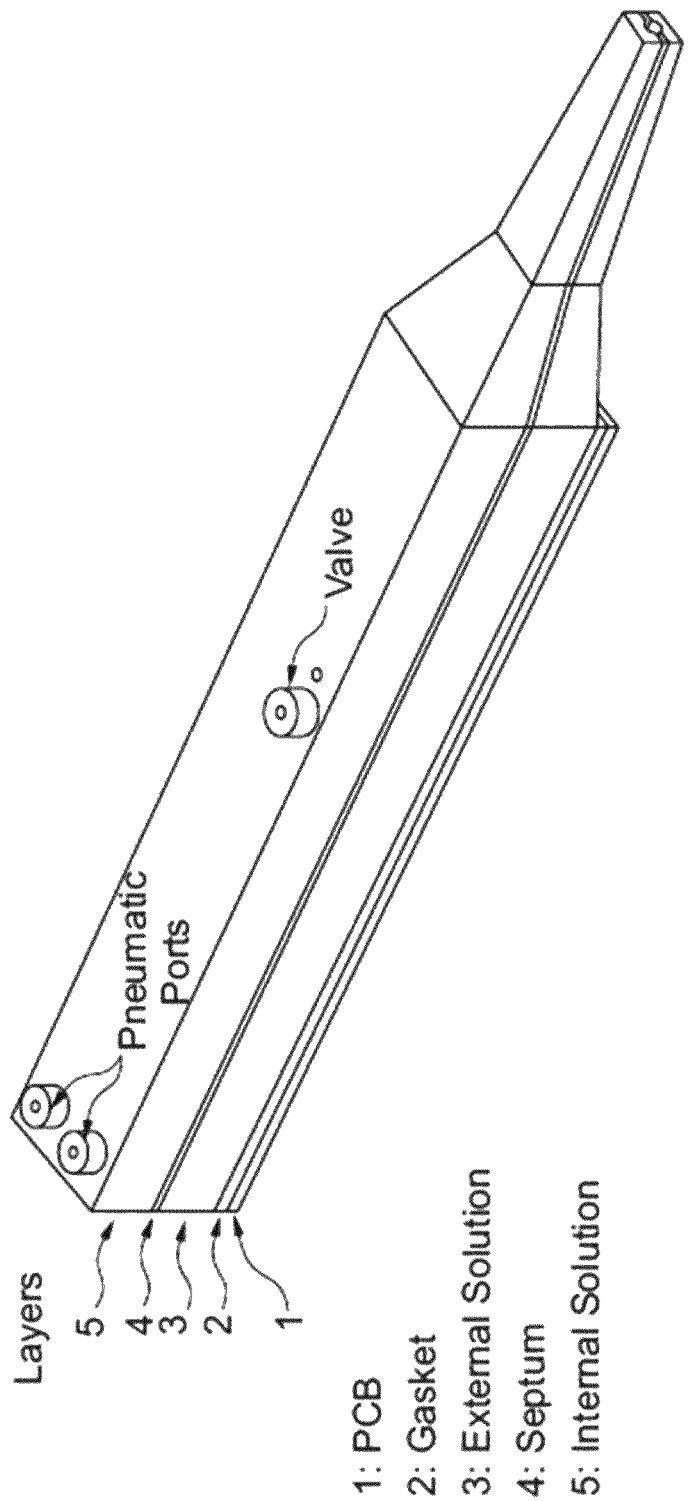
FIG. 3 is an illustration of pipette tip of the handheld device of the present invention.
Figure 3A:
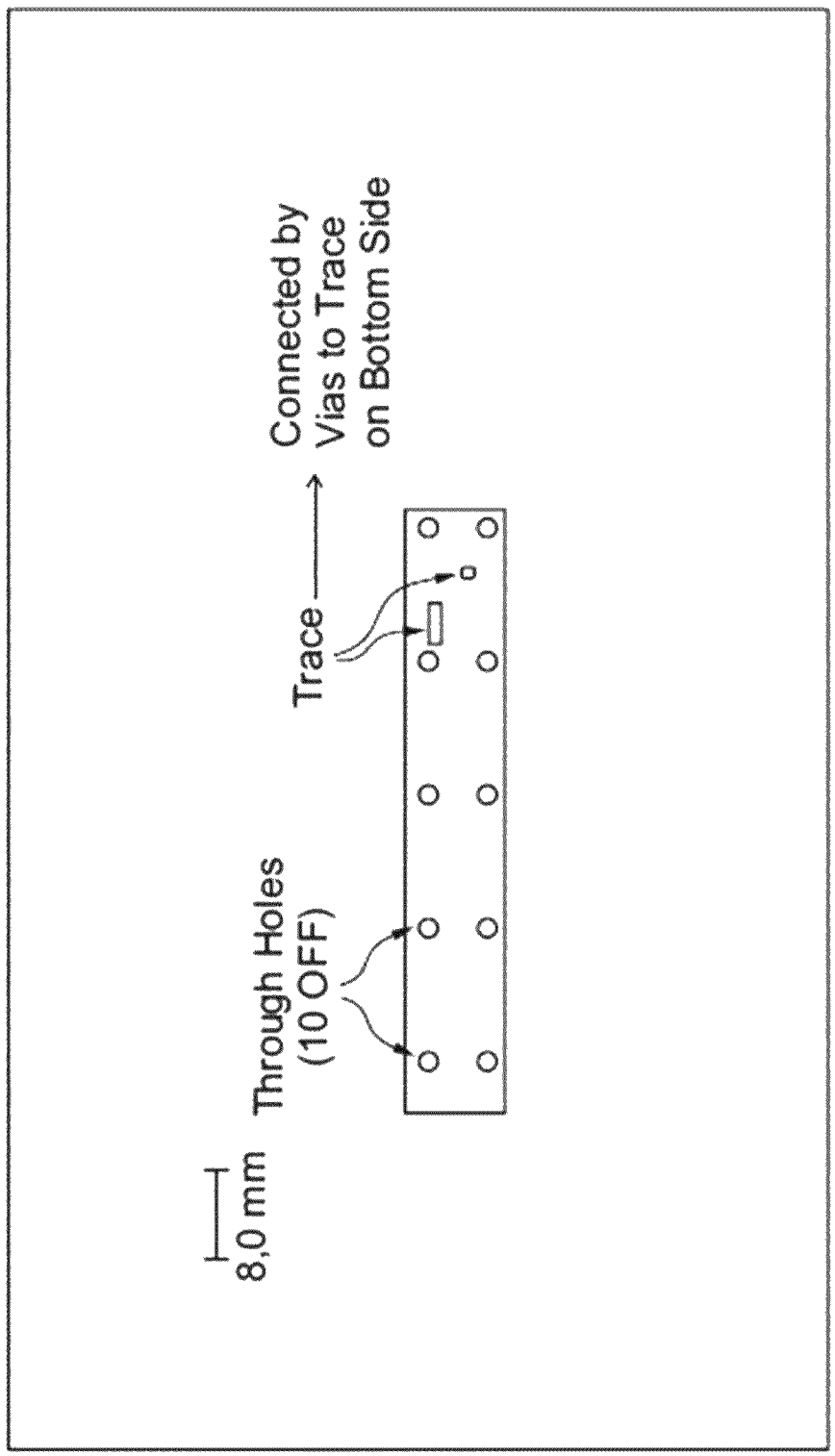
FIG. 3a is an illustration of a PCB layer of the pipette tip of FIG. 3.
Figure 3B:
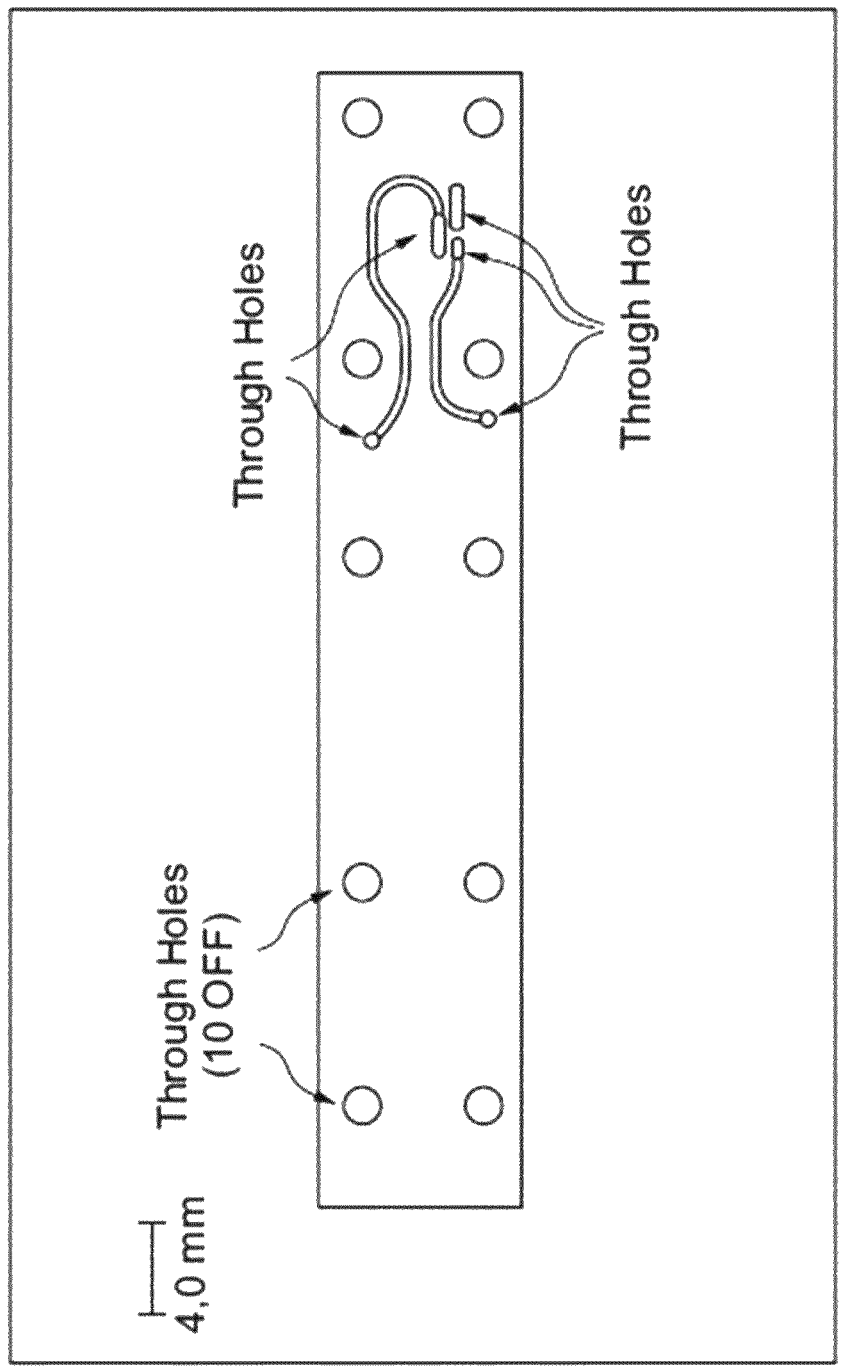
FIG. 3b is an illustration of the under side of a gasket of the pipette tip of FIG. 3.
Figure 3C:
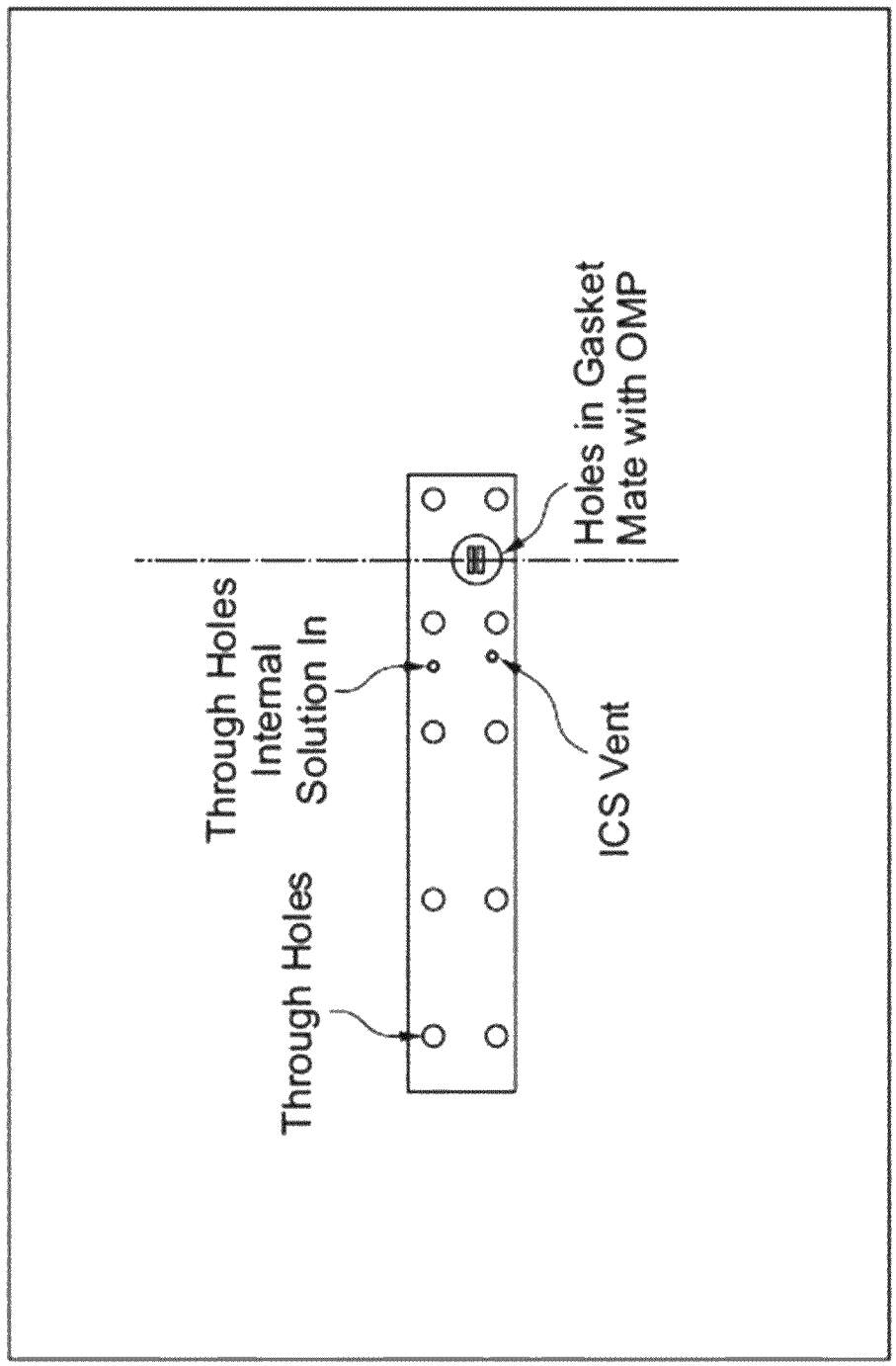
FIG. 3c is an illustration of the upper side of the gasket of the pipette tip of FIG. 3.
Figure 3D:
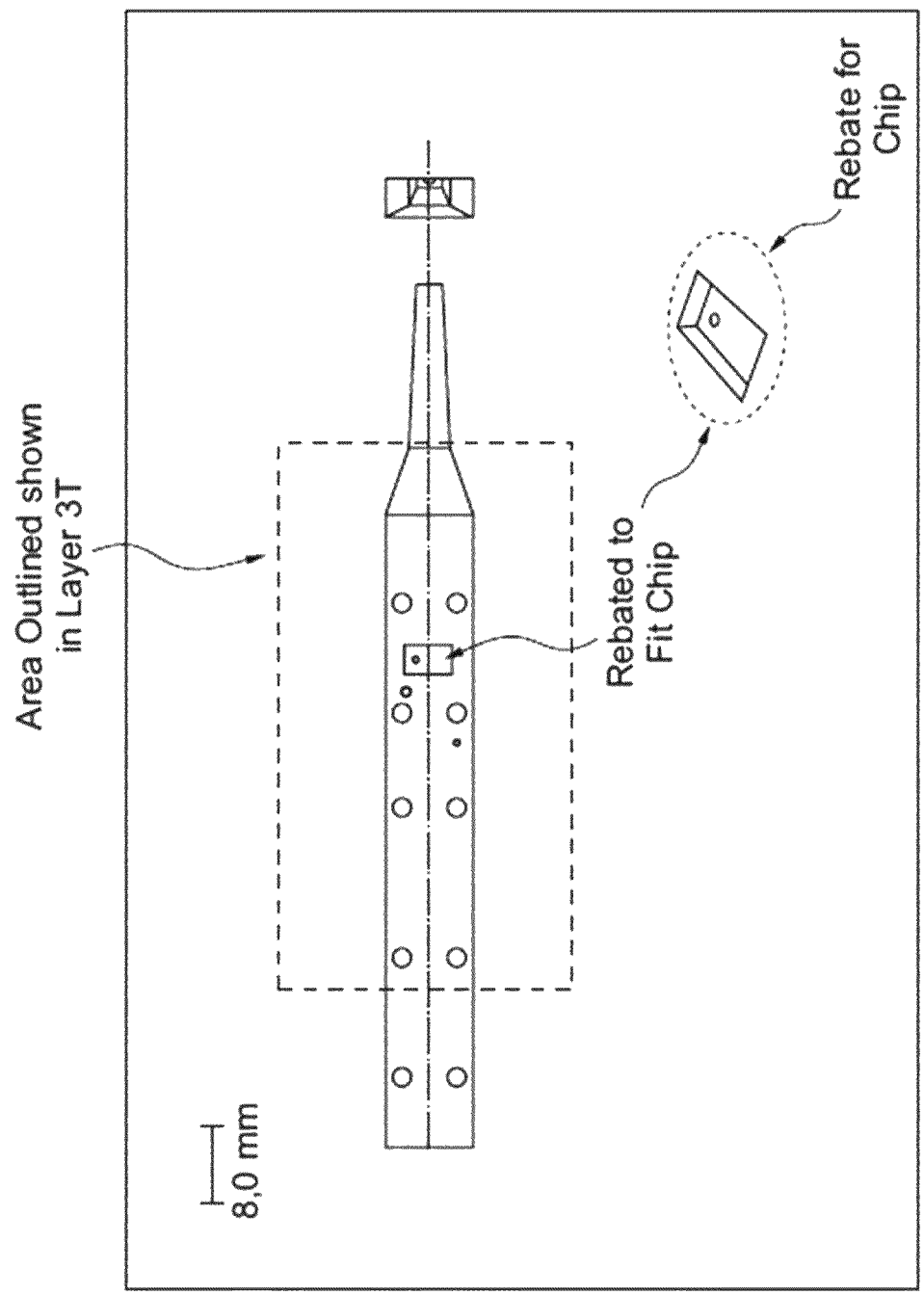
FIG. 3d is an illustration of an external layer of the pipette tip of FIG. 3.
Figure 3E:
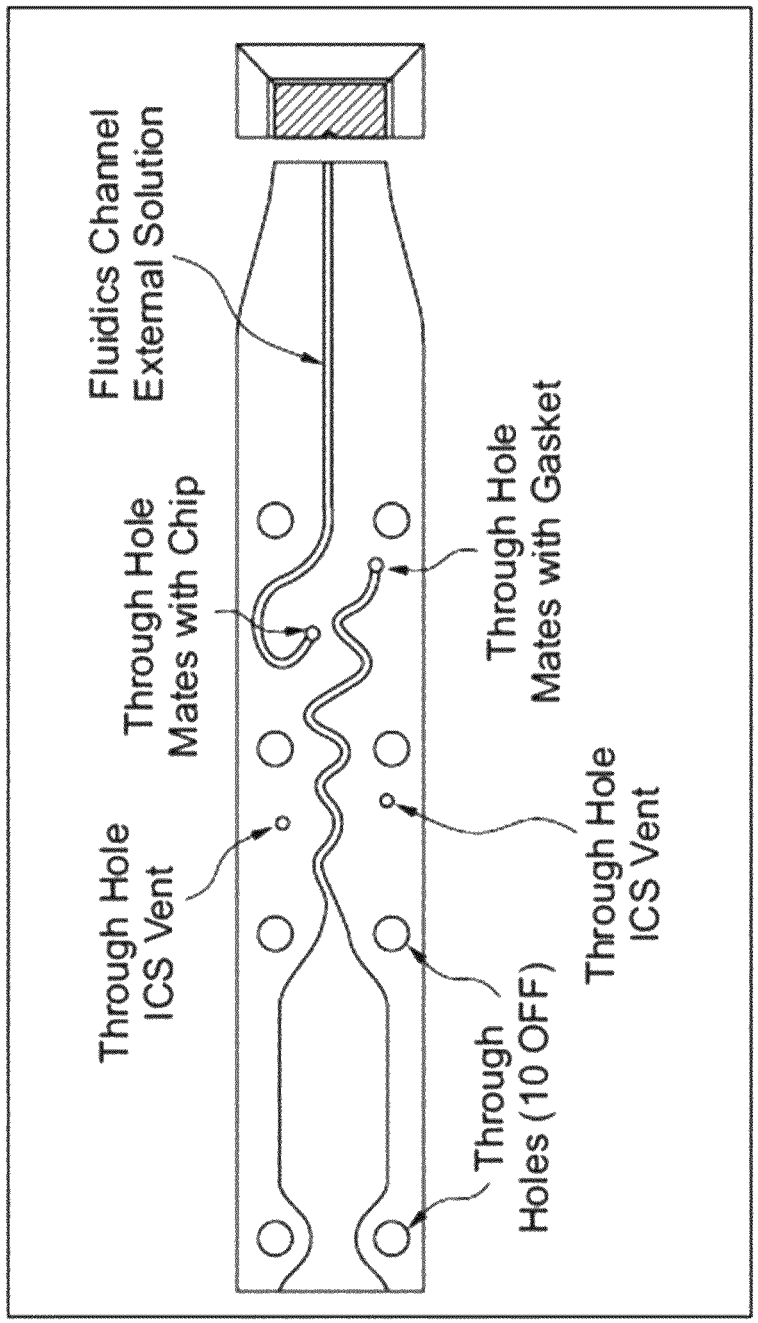
FIG. 3e is an illustration of the external layer with fluidics channels.
Figure 3F:
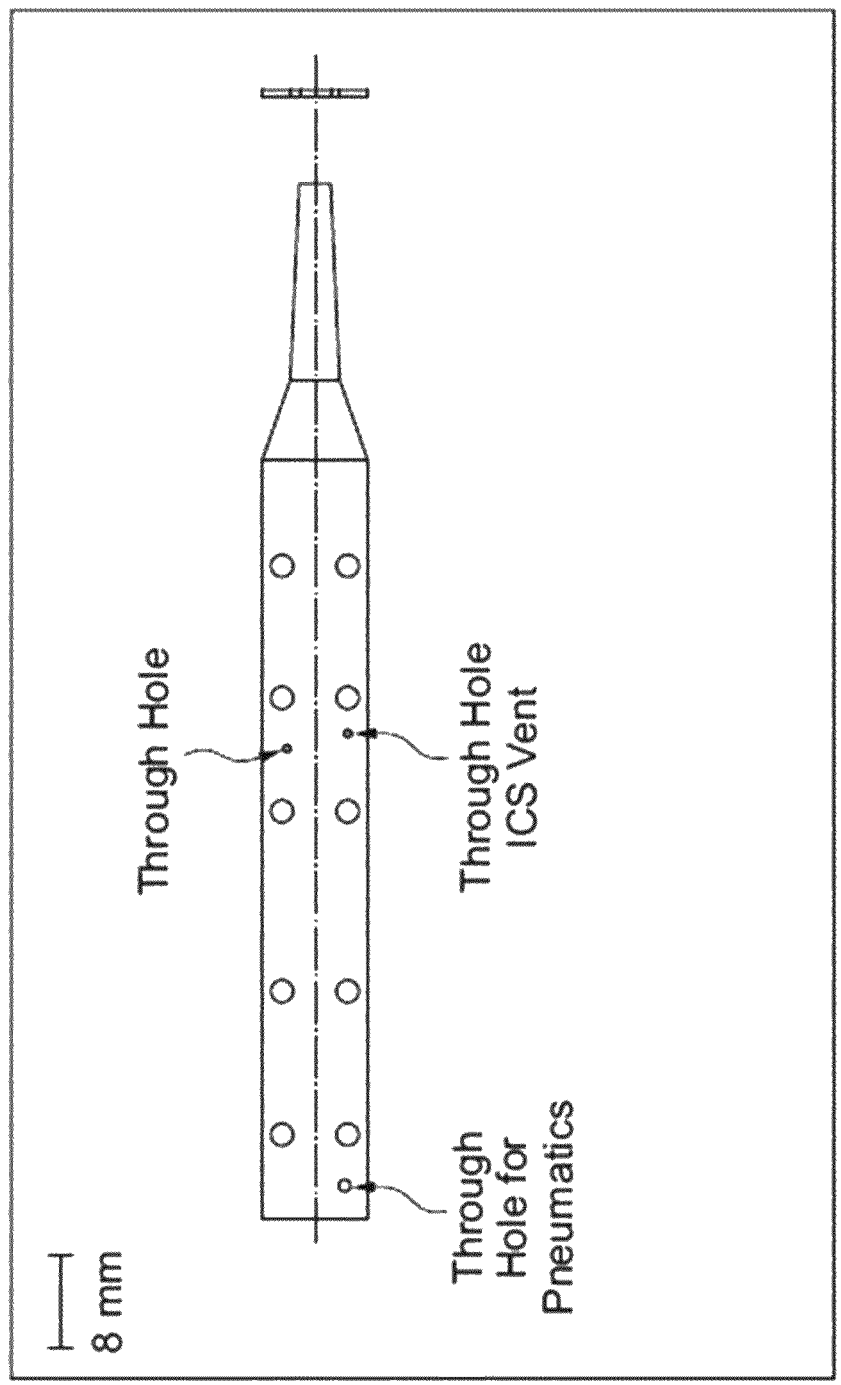
FIG. 3f is an illustration of a septum dividing internal and external solution layers.
Figure 3G:
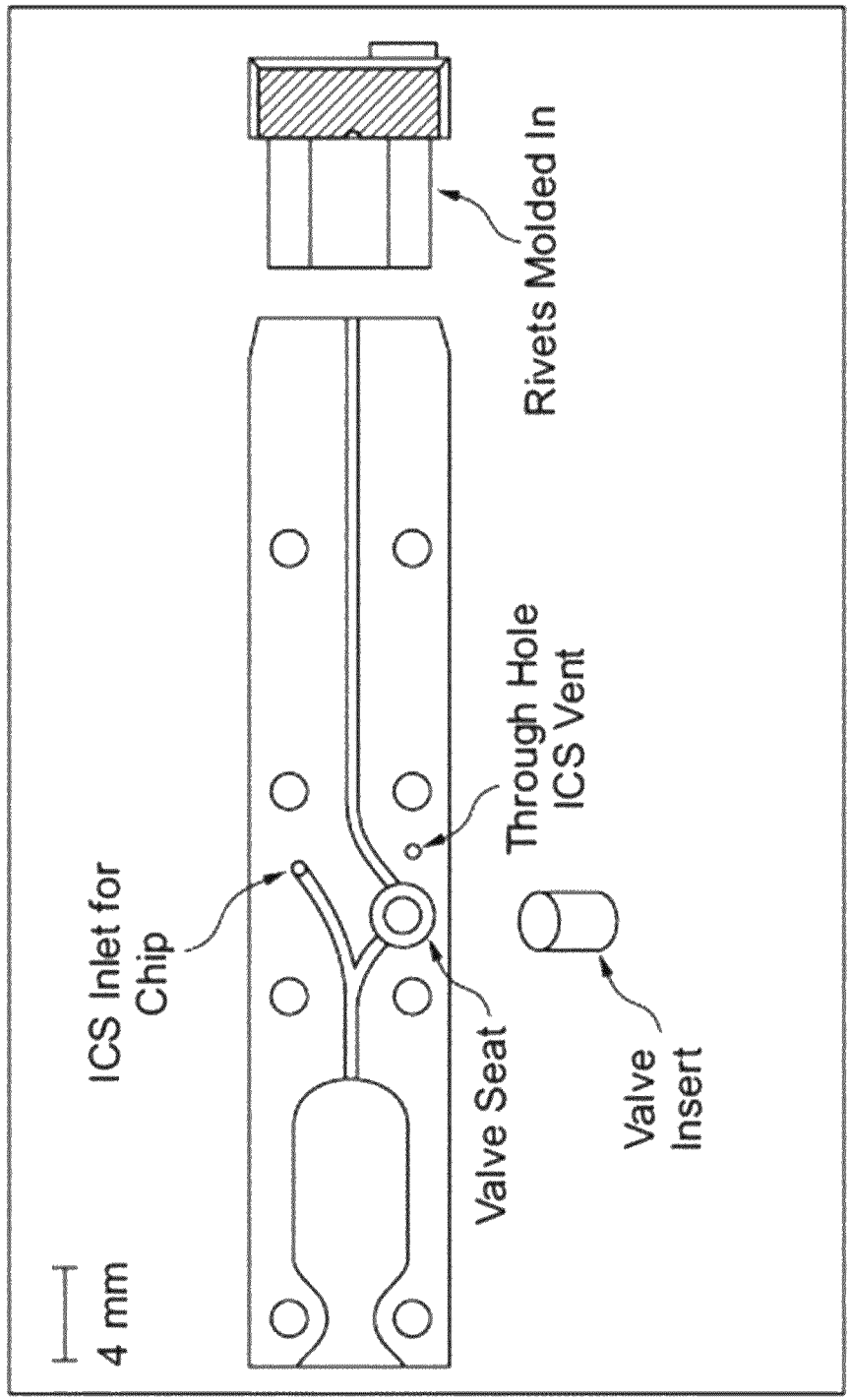
FIG. 3g is an illustration of the internal solution layer containing fluidics channels and valve to allow internal solution to be isolated from the pipette.

Embodiments of the present invention provide a portable handheld device for electrophysiological measurements that performs the tasks of a laboratory floor or bench model patch clamp apparatus. The device is generally depicted in FIGS. 1 and 2. Specifically, an ion channel-containing lipid membrane may be positioned at a site by using pressure driven flow in a fluidics channel with an ionic solution containing the ion channel-containing lipid membrane.

Hence, in one aspect, the present invention provides a substrate for determination and/or monitoring of electrophysiological properties of ion channels in ion channel-containing lipid membranes, said substrate comprising: a first site for holding ion channel-containing lipid membranes, the site comprising one or more passages in the substrate, a first end of said passage being in contact with a first domain at a first upper surface part of the substrate and a second end of said passage being in contact with a second domain in a first canal, a reference electrode in electrical contact with the first domain, a working electrode in electrical contact with the second domain, and the second end of said passage and the first canal being dimensioned so that a flow of an ionic solution in the first canal can generate a flow through said passage from the first domain into the second domain or vice versa, and the first end part of said passage being adapted to form a seal with an ion channel-containing lipid membrane held at the site or sites in the case of a multihole substrate. The substrate, the seal and the lipid membrane thereby separating the first domain of the site from the second domain so that one or more electrical properties of the membrane can be determined and/or monitored by determining and/or monitoring an electrical signal between the reference electrode and the working electrode.

Preferably, the dimensions and material composition of the first end parts of the passages are adapted to provide high electrical resistance seals between an ion channel-containing lipid membrane held at a site and the substrate. In the present context, a high electrical resistance seal means that the electrical resistance along a path between the adjoining surfaces of the substrate and the membrane is of the order of 10 M$\Omega$ or larger, preferably larger than 100 M$\Omega$ or 1 G$\Omega$, also known as a giga seal.

The canal may be formed in the substrate or consist of a groove formed in a surface part of the substrate which is subsequently closed by arranging another substrate on said surface part thereby forming a canal or pipe.

The substrate may comprise further sites with passages having end parts in contact with the first and second domains. Thus, more than one site may share the first canal whereby the flow generated in the first canal can be used to control a flow in several passages in parallel.

The substrate preferably further comprises a first end part to the canal for introduction of an ionic solution in the canal.

Hence, the dimensions of the canal and the first end part of the canal as well as the dimensions and positions of the electrodes in contact with the second domain are preferably adapted so as for an ionic solution introduced through the first end part to form electrical contact with the electrodes in contact with the second domain. In order to assist introduction of an ionic solution in to the canal, the substrate may further comprise one or more regions of hydrophilic or hydrophobic material arranged in relation to the canal, in the canal, or in the first end part of the canal.

Preferably, the ion channel-containing lipid membrane forms a high electrical resistance seal, such as a giga-seal, with the first end of the passage so that one or more electrical properties of the membrane can be determined and/or monitored by determining and/or monitoring an electrical signal between the electrodes generating the flow.

After establishment of the high electrical resistance seal, the method preferably comprises the step of checking the high electrical resistance seal between an ion channel-containing membrane held at a site and the first end of the passage by successively applying a first electric potential difference between the working electrode and the reference electrode and monitoring a first current flowing between the working electrode and the reference electrode. If the first current is smaller than or equal to a predetermined threshold current, then the site may be approved as having an acceptable seal between the ion cannel-containing structure and the first end of the passage. This method step is used to determine the character of the established seal. If there is no giga-seal, then a large leak current will flow between the membrane and the site. If a giga-seal is established, the current is primarily drawn through the membrane and will be significantly smaller than the leak current.

Also, after establishment of the high electrical resistance seal, the method preferably comprises the step of establishing a whole-cell configuration by rupturing the part of the ion channel-containing membrane, which is closest to the working electrode. The rupturing of the part of the membrane may be performed by the application of pressure pulses or ramps or by applying a series of voltage pulses between the working electrode and the reference electrode across the area of membrane forming the patch. The rupture of the membrane may be determined by monitoring a current flowing between the working electrode and the reference electrode, when this current exceeds a predetermined threshold value, the membrane has been ruptured allowing electrical and fluid connection with the cell interior.

In an embodiment of the invention, the handheld device of the present invention has two main components:
1. A handheld body (also referred to herein as a pipette body) comprised of a control button and a display, a head stage and an amplifier, pumps and valves, pneumatics/fluidics controller, pneumatic connections and a USB interface USB or Ethernet or other serial interface.
2. A pipette tip comprised of a one or more layers wherein one of said layers comprises electrodes capable of making an electrical connection between 1 or more fluids. Said pipette tip may also include a gasket with fluidics channels, a layer with extra cellular fluidics channels, a septum dividing extra and intracellular fluidics layers, a layer with intracellular fluidics channels.

The Handheld Body

The handheld body may comprise an aluminum frame core and molded plastic components for both the internal and external structure. The aluminum frame will be used for components that require structural rigidity and precision, for example, the clamp mechanism for the pipette tip. Shielding to prevent electrical interference from outside the device and prevent radiation from the device will be required. The body may be composed of plastic coated internally with a layer of high quality conductor to act as a Faraday cage. The Faraday cage will act as a "floating earth/ground connection" and shield the internal electronics from electrical noise. The device will be constructed to meet current EMI radiation standards for portable laboratory devices using conductive seals where required. The external surface will be insulated and precautions will be taken to reduce/eliminate capacitive coupling between the user and the internal electronic components. Within the device, the recording circuit (comprising the head stage electronics and digitizer) will be mounted away from other components, e.g. pumps, embedded computer, microprocessor, and LCD screen, that generate significant amounts of electromagnetic radiation during operation and the connection with the pipette tip will be kept as short as possible to limit noise pick-up and input capacitance. The clamping mechanism for the pipette tip will be conductive (likely aluminum) and electrically contiguous with the Faraday cage. The internal frame, which will be connected to the "Faraday cage" may also serve as a shield to isolate these components from each other. In addition to the electrical requirements, the device must be light enough to operate with one hand without fatigue or risk of repetitive strain injury. The internal aluminum frame will be used also for heat dissipation and a conductive route for heat to the external surface of the device will likely be required. Batteries will be contained within the molded handle together with additional electronics. The base of the handle may be used to rest the device and as a means of heat radiation. A means for external electrical connection for battery charging and connection to a computer will be provided on the outer case. The electrical connectors for the tip will be made of low resistance contacts suitable for repetitive use and easily replaced if damaged either mechanically or by contamination with liquids e.g. salt solution. There will be vent holes at the bottom of the device to allow exhaust of the small volumes of air moved by the internal pumps during the operation of the device.

Handheld Body Assembly

In one embodiment, the body of the pipette comprises two molded halves into which the internal frame will fit. Some components will be bolted to the frame directly and others to the plastic case/body. Within the molded plastic body, threaded mounting points will be provided and the molding will be strengthened in areas that may be stressed by weight (e.g. at the handle) or presence of screws. The internal structure will also be divided by conductive plastic to provide shielding of electronic components. Anti-vibration mountings may be used for motors.

The Pipette Tip

In one embodiment, the pipette tip is a key component of the present invention. Said pipette tip may be comprised of one or more layers. The pipette tip is where the electrical connection, between the fluids and the measuring instrumentation, is made.

In an embodiment of the invention, the pipette tip comprises a planar chip, with holes for patch clamping membranes, made from silicon. The processes for the manufacture of said silicon chip is generally disclosed in WO 03/089564 to Sophion Bioscience A/S, which is incorporated hereby by reference.

In one embodiment of the invention, the electrical connection between fluids and instrumentation can be done via electrodes printed or deposited on a Printed Circuit Board (PCB). Also, said electrodes can be held in contact with said fluids by a Ag/AgCl wire held in the solution. Further, said electrodes can be printed directly onto the layers with the fluidics channels.

In an embodiment of the PipetteTip, the user will be able to apply multiple internal solutions. The internal side of the printed circuit board in the tip would be connected to the fluidics channels normally used for external solution.

In yet another embodiment of the Pipette Tip, the use of microfluidics channels in the extra and intracellular layers facilitates the automated dilution of the test solutions using laminar flow In another embodiment of the pipette tip, said tip may comprise three layers. By way of non-limiting example, layer 1 may contain fluidics channels (molded, machined or other) and may have Ag/AgCl electrodes printed onto part of the fluidics channels. This layer is for internal or external physiological solution.

Layer 2 provides a septum/dividing wall that is ether perforated with one or more holes (with a diameter of 1-5 $\mu$m) suitable for patch clamp or to which a patch clamp chip (with one or more holes of a diameter of 1-5 $\mu$m) has been bonded. Ag/AgCl electrodes may be printed onto this layer.

Layer 3 contains fluidics (molded, machined or other) and may have Ag/AgCl electrodes printed onto part of the fluidics channels. This layer is for internal or external physiological solution.

In a further embodiment of the pipette tip as shown in FIGS. 3 and 3a-3g, the tip comprises five layers to allow independent fluidics and pneumatic control of the external and internal solution flow and pressure on each side of the planar patch chip. Internal and external solution is moved through microfluidic channels molded into the plastic components that comprise the layers.

Layer 1—PCB layer containing the Ag/AgCl electrodes that make contact with the internal and external solution. The electrodes are connected by via through the PCB to traces that may be used to connect to the patch clamp amplifier/I/V convertor.

Layer 2—Gasket Layer containing molded fluidics channels and, after assembly, is pressed tightly against the chip and the adjacent plastic "extracellular" layer (diagram: Layer 3B) to obtain a liquid/gas tight seal.

Layer 3—The extra cellular layer containing molded fluidics channels and through holes. The channels provide a pathway for extracellular solution to flow on the top surface of the chip (above the patching hole) and into a waste reservoir.

Layer 4—The septum layer providing fluidics and electrical isolation between the fluidics channels in the extracellular layer and the intracellular layer.

Layer 5—The intracellular layer containing molded fluidics channels and through holes. The channels provide a pathway for extracellular solution to flow on the bottom surface of the chip (below the patching hole) and into a waste reservoir. A valve is present in order to allow the fluidics channels containing internal solution to be isolated from the end of the tip.

Figure 4:
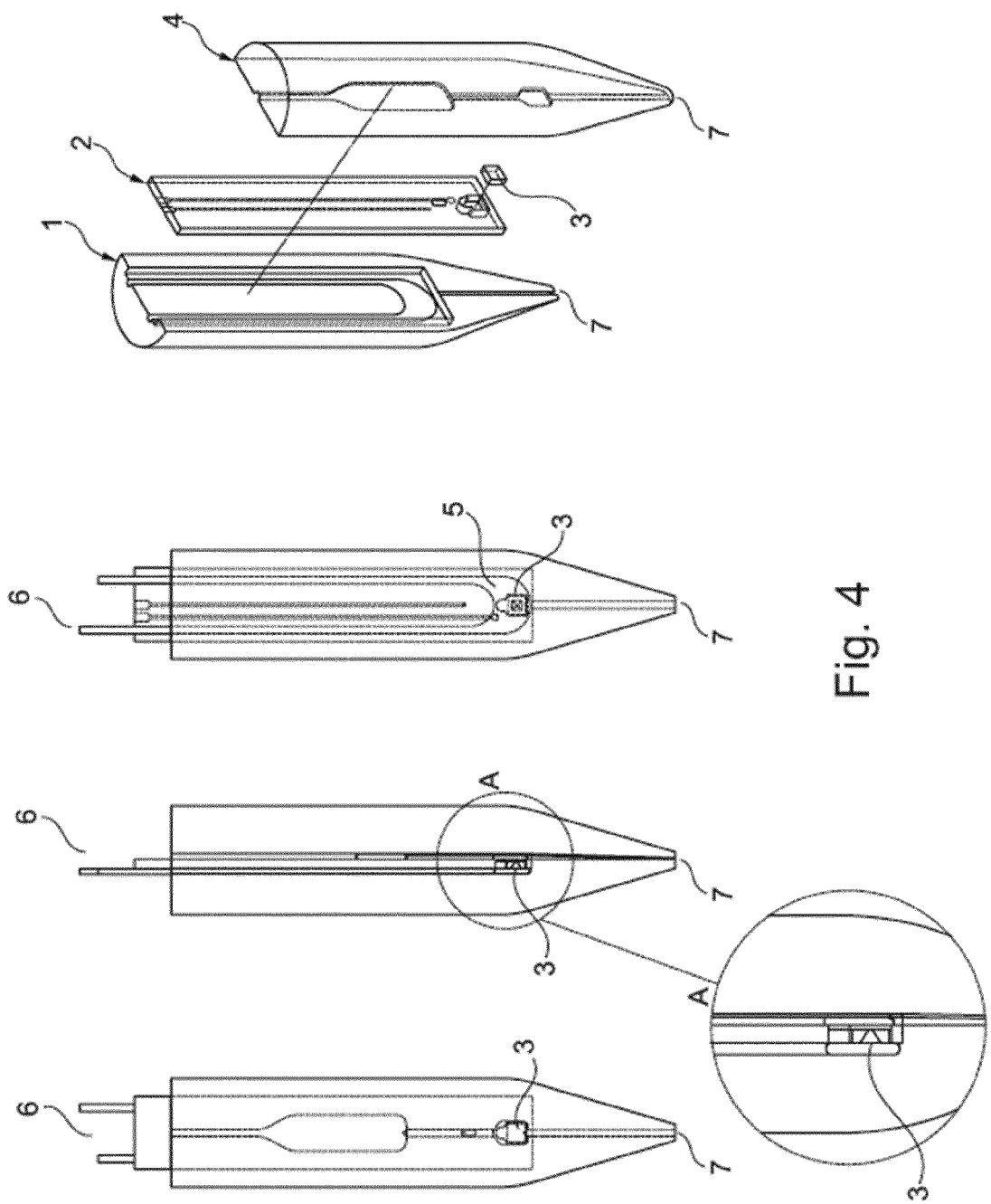
FIGS. 4 and 5 show respective embodiments of further embodiments of a pipette tip of a handheld device according to the present invention.
Figure 5:
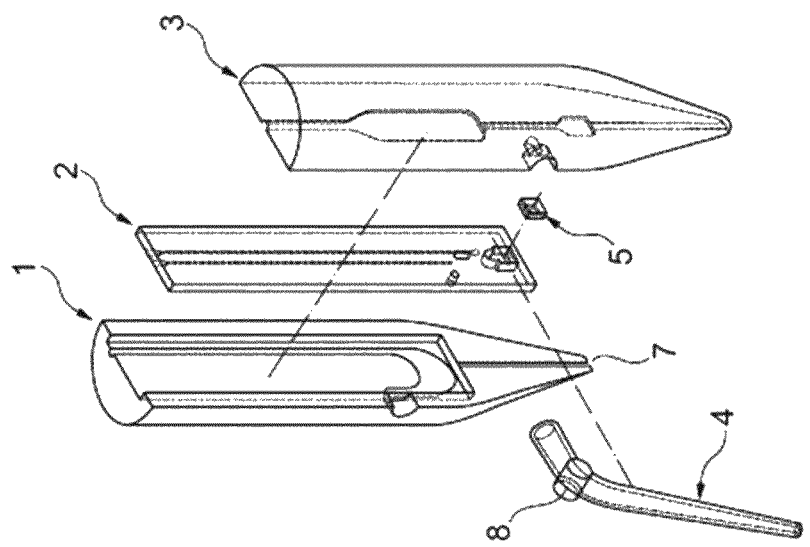
Figure 5:
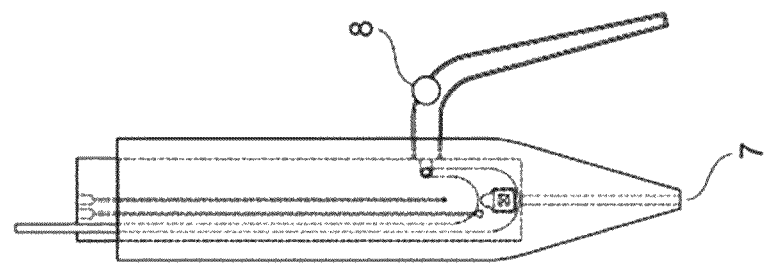
Figure 5:
Figure 5:
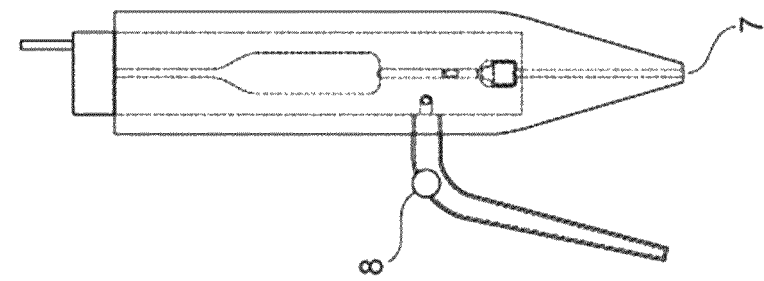

FIGS. 4 and 5 discloses alternative embodiments of a pipette tip comprising respective housing and channel parts 1 and 4 (FIG. 4), and 1 and 3 (FIG. 5), respectively. Printed Circuit Board (PCB) layer 2 is provided and carries substrate 3 (FIG. 4) and 5 (FIG. 5), respectively, which is printed onto PCB 2.

FIG. 4 discloses an embodiment of a pipette tip according to one embodiment of the invention. The microfluidic analysis substrate is provided at 3. Before the pipette tip is attached to the handheld body (not shown), intracellular fluid is aspirated into pathway or compartment 5, e.g. by attachment of an external aspiration device (not shown) at 6. Next, the pipette tip is attached to the handheld body, which is operated according to the method of the present invention. Thereby the fluid including the ion channel containing lipid cellular membrane is aspirated into the pipette tip at 7.

FIG. 5 discloses an embodiment of a pipette tip according to another embodiment of the invention. The pipette tip comprises a disposable aspiration part for aspiration of aspirating intracellular fluid in the pipette tip. A duct within the disposable aspiration part is connected to a suitably configured aspiration device within the handheld body (not shown). In operation, the pipette tip is initially mounted to the handheld body, which is subsequently operated to aspirate intracellular fluid into the disposable aspiration part and further into the pipette tip. The disposable aspiration part comprises a bending section at 8, allowing it to be bent relative to the remained of the pipette tip once intracellular fluid aspiration has been completed. The bending section 8 serves as a valve to close the duct for intracellular fluid. Subsequently the handheld body is operated to aspirate the fluid including the ion channel containing lipid cellular membrane is aspirated into the pipette tip at 7.

Figure 6:
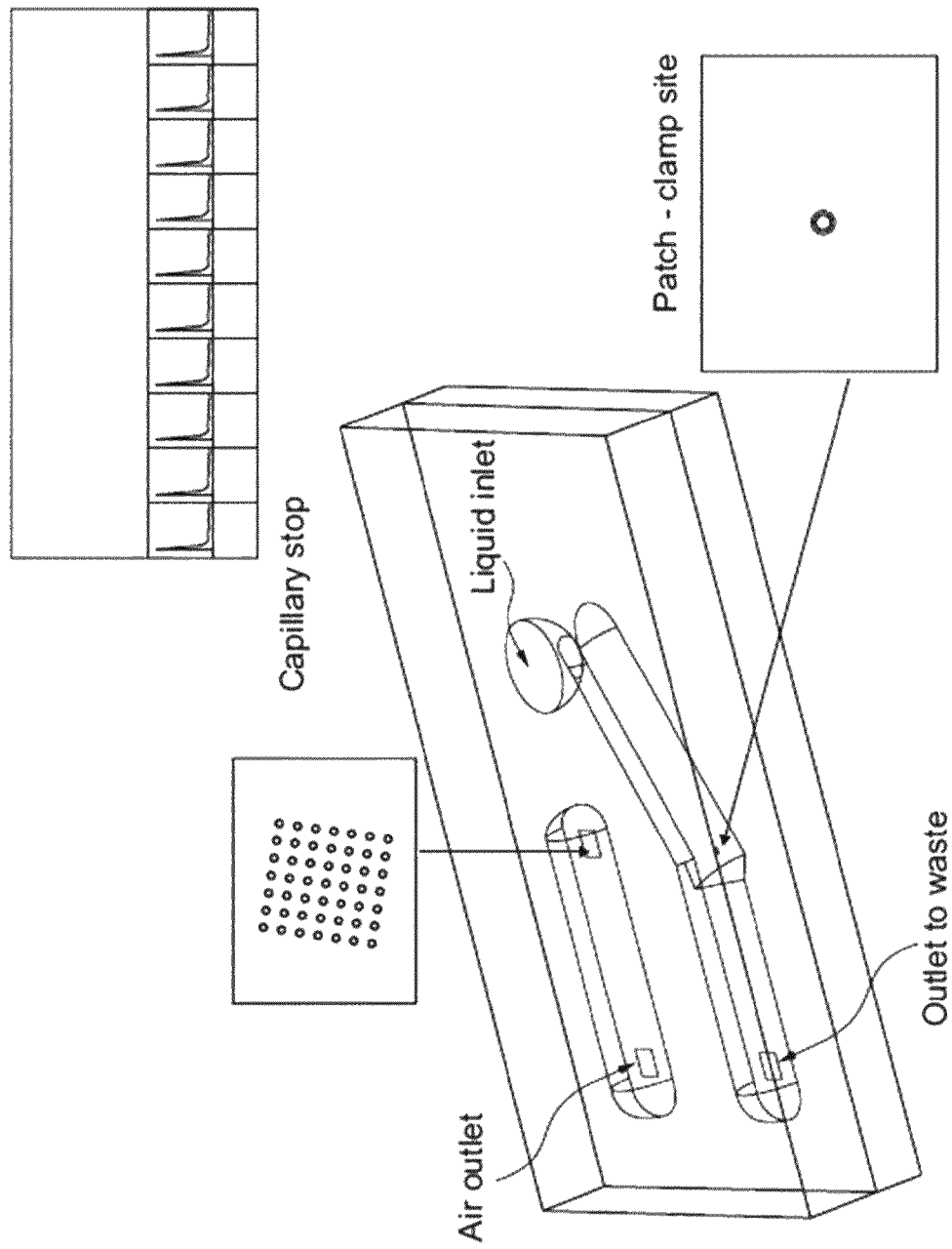
FIGS. 6 and 7 illustrate a substrate for patch-clamp analysis in an embodiment of the handheld device according to the present invention.
Figure 7:
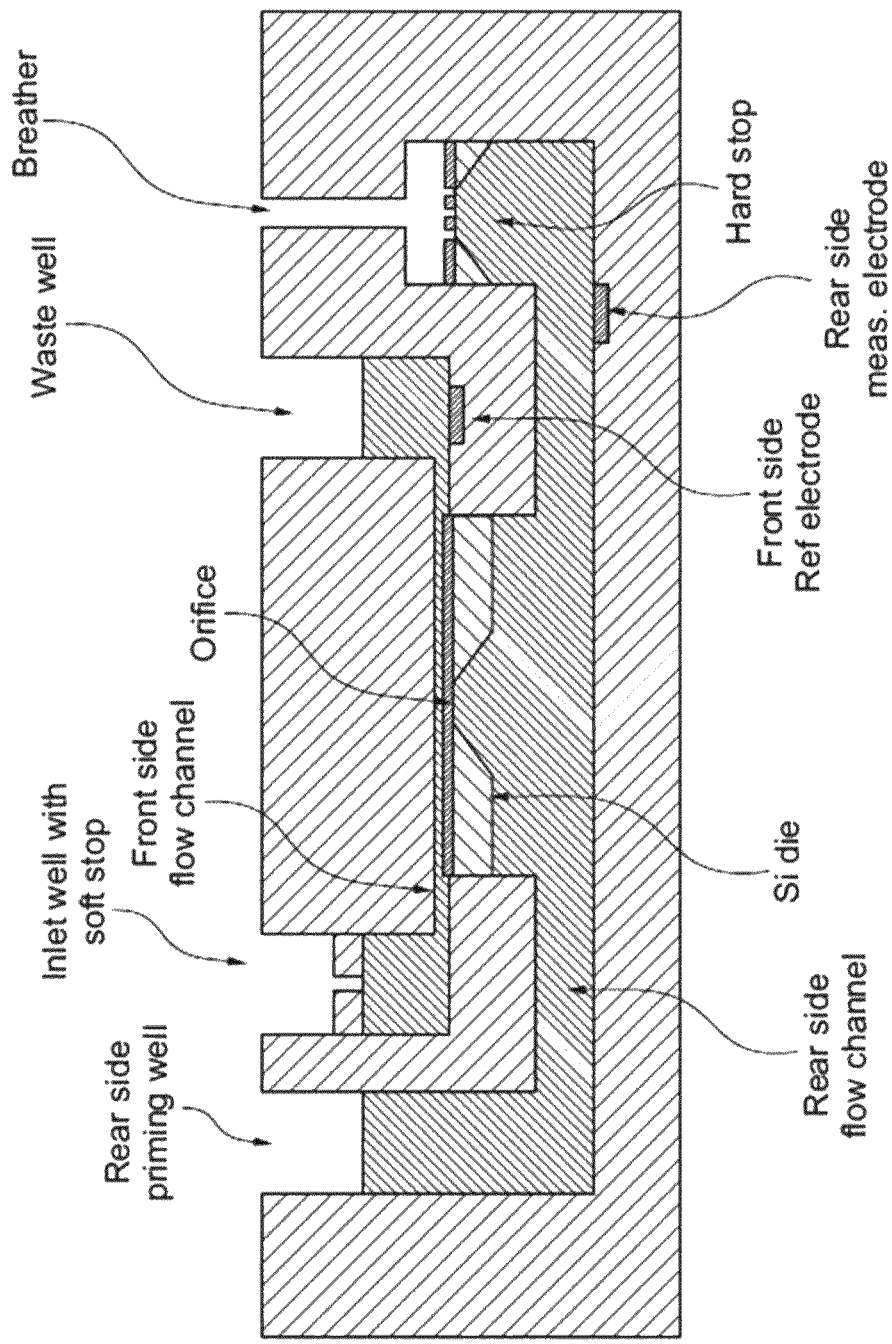

FIGS. 6 and 7 disclose an embodiment of a substrate for microfluidic analysis, suitable for the method, device and disposable pipette tip according to the invention.

Figure 8:
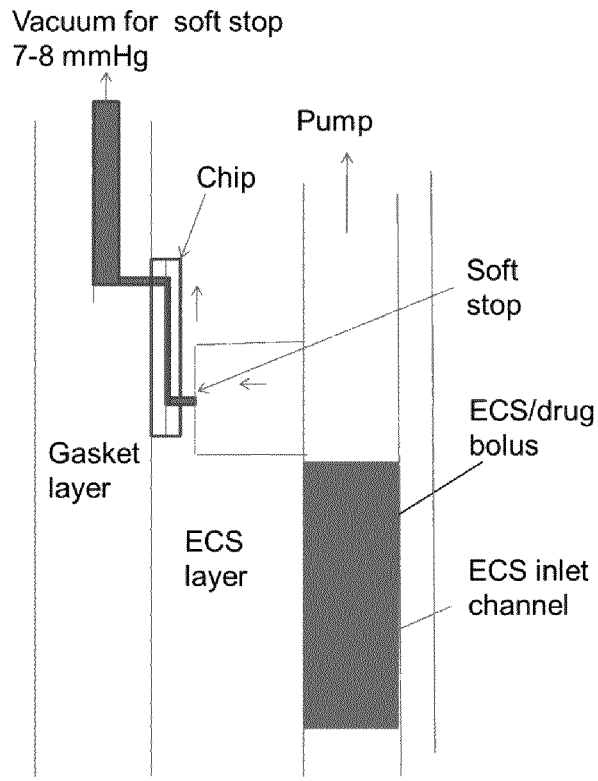
FIGS. 8 and 9 illustrate the operating principle of a so-called soft stop incorporated in an embodiment of the pipette tip according to the present invention for facilitating aspiration and/or sampling of liquid.
Figure 9:
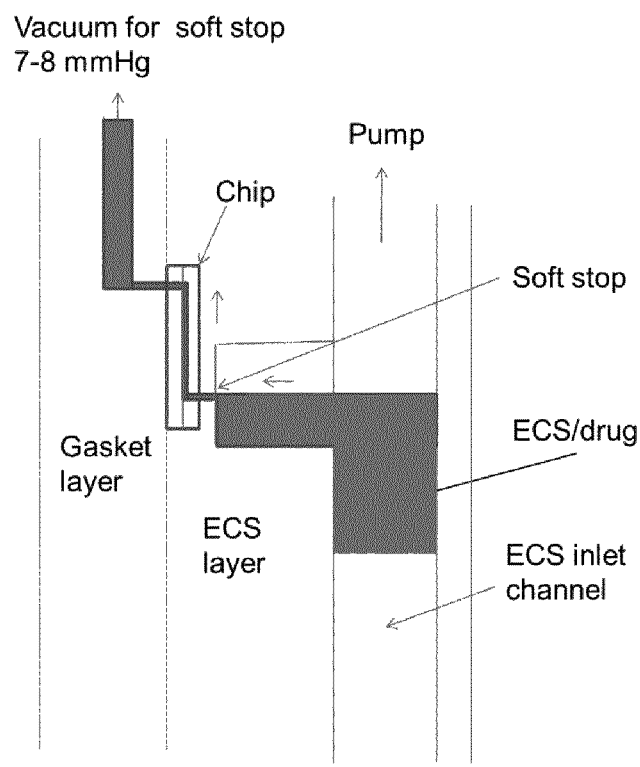

FIGS. 8 and 9 illustrate the operating principle of a so-called soft stop which may be incorporated in an embodiment of the pipette tip according to the present invention.

Operation of an Embodiment of the Present Invention

Experiment design and patch protocol are entered into a GUI running on a computer (the "Server") and downloaded to the handheld via USB or Ethernet or other serial interface. An LCD screen on handheld body displays the sequence of steps for the experiment. The next step in the sequence is highlighted on the display. The user-operated button on the handheld body is currently disabled.

A pipette tip is loaded manually and the button is enabled by appropriate software.

A button on the handheld body is pressed to trigger aspiration of internal solution. During aspiration, the fluid is pumped, via fluidic channels in the intracellular layer of the tip, through the underside of the patch chip and into the internal solution waste reservoir. The user is prompted to remove the pipette tip from the internal solution, the button is disabled and valve on the handheld body is closed to seal the intracellular fluidics pathway. The pressure protocol for filling with internal solution is activated and the hole in the patch chip is filled while displacing air through a capillary stop in the chip.

The user is prompted for filling with external solution and the button is activated. Pressing the button aspirates external solution that passes over the top surface (cell side) of the chip. The fill button is disabled and the system pauses to allow stabilization of the recording electrodes in the tip.

Junction null is performed and electrode resistance is checked. A default setting for electrode capacitance compensation is used. If the electrode resistance is acceptable, the user is prompted for cell suspension and the fill button is enabled to allow cell suspension to be aspirated.

A fill button is disabled and a patching protocol is started. The protocol (loaded previously from the computer) is implemented under the control of the embedded computer/processor in the device.

As the experiment starts, the user is prompted to start the pre-loaded compound addition protocol. Alternatively, the user may be prompted to start an experiment that has not been preloaded but rather, each time liquid is aspirated, the recording is labelled (flagged) for analysis.

Electrical System

The electrical system for measuring of electrical properties of membranes on the substrate, hereafter the main circuit, comprises one or more working electrodes present at each measuring site and a reference electrode in contact with each site.

The or each pair of working-reference electrodes is connected to one or more amplifiers and a low noise current to voltage converter. The output from the current to voltage converter is filtered, digitized and raw data stored in the device prior to uploading to a server. The instrumentation in embodiments of the device may be capable of standard patch clamp compensations/corrections such as fast capacitance compensation, junction nulling/junction potential offset, slow capacitance compensation, series resistance compensation.

Soft Stop

The term soft-stop refers to a small hole in the extracellular fluidics pathway to the chip (or substrate) that selectively allows solution but not air to pass under a driving force provided by a small pressure difference. The walls of the soft-stop are hydrophilic to enhance the adhesive force with aqueous solution. The soft-stop in the of the pipette tip is positioned 90 degrees approximately from the flow channel for the extracellular solution.

In order to reduce the volume of extracellular solution required to exchange the contents of the extracellular flow channel in the chip, a soft-stop may be incorporated into the design of the pipette tip. Reducing the amount of extracellular solution added is desirable because of the limited volume in the waste reservoir which determines how many compound additions can be made. The soft stop allows the aspiration volume to be less than the dead volume in the incoming flow channel, see FIGS. 8 and 9.

Referring to FIG. 8, the pump of the handheld device (not shown) is switched on briefly to aspirate a small volume (bolus) of solution. Then the pipette tip is removed from solution and the pump is restarted to move the bolus over the soft-stop.

As shown in FIG. 9, the bolus reaches the soft-stop which breaks allowing exchange of solution.

The invention claimed is:

1. A disposable pipette tip for a handheld device for analysis of electrophysiological properties of a cellular membrane ion channel in an ion channel containing lipid cellular membrane, said handheld device comprising a handheld body with a housing including a pump and an electronic controller, the disposable pipette tip comprising a pathway for fluid, said pathway connecting an open end of the pipette tip to an analysis substrate adapted to transmit an electrical current through the ion channel in said ion channel-containing lipid cellular membrane, when said lipid cellular membrane is held at a predetermined site of the substrate; the disposable pipette tip being configured to be releasably attached to the body of said handheld device, with the open end of the pipette tip being exposed to an exterior environment, and to provide a hydraulic connection between the pump of the handheld body and said pathway, and to provide an electric connection between the electronic controller and at least one electrode of the substrate.

2. The disposable pipette tip according to claim 1, wherein said substrate is a patch clamp electrode unit, and wherein the at least one electrode comprises electrodes for contacting test solutions.

3. The disposable pipette tip according to claim 2, wherein the pipette tip comprises a laminate structure comprising a plurality of layers, wherein one of said layers comprises the at least one electrode, and wherein another one of said layers comprises at least one flow channel for at least one fluid.

4. The disposable pipette tip according to claim 3, wherein:
a first one of said layers comprises electrodes for contacting internal and external test solutions;
a third one of said layers comprises an external solution layer comprising channels to facilitate the movement of an external test solution on the top surface of said first layer and into a waste reservoir;
a fourth one of said layers comprises an internal solution layer comprising channels to facilitate the movement of said external test solution on the bottom surface of said first layer and into a waste reservoir.

5. The disposable pipette tip according to claim 4, wherein said first layer comprises a printed circuit board.

6. The disposable pipette tip according to claim 4, further comprising a second layer comprising a gasket between said first and said third layers.

7. The disposable pipette tip according to claim 4, wherein a valve is present in said fourth layer to isolate said internal test solution.

8. The disposable pipette tip according to claim 4, wherein said third layer is separated from said fourth layer by a septum.

9. The disposable pipette tip according to claim 1, further comprising a duct for aspirating intracellular fluid into the pipette tip.

10. The disposable pipette tip according to claim 9, wherein said duct is connectable to an external aspirating device when the pipette tip is separate from the handheld body of said handheld device.

11. The disposable pipette tip according to claim 9, wherein said duct is connectable to an aspirating device housed within the handheld body of said handheld device, when the pipette tip is connected to the handheld device.

12. The disposable pipette tip according to claim 9, wherein said duct is provided in an aspiration pipe protruding from the remainder of the pipette tip, and wherein said aspiration pipe is connected to the remainder of the pipette tip through a valve structure.

13. The disposable pipette tip according to claim 12, wherein said valve structure comprises a bending section allowing the aspiration tip to be closed off relative to the remainder of the pipette tip by bending thereof by hand.

14. The disposable pipette tip according to claim 1, wherein said substrate is printed onto a printed circuit board (PCB) carrying electric connectors for the electrodes of the substrate.

15. A handheld device for analysis of electrophysiological properties of a cellular membrane ion channel in an ion channel containing lipid cellular membrane, the device comprising:
a handheld body comprising a housing including a pump and an electronic controller;
a disposable pipette tip according to claim 1;
the handheld body and the disposable pipette tip being configured to releasably attach the pipette tip to the body with the open end of the pipette tip being exposed to an exterior environment, to provide a hydraulic connection between the pump of the handheld body and said pathway, and to provide an electric connection between the electronic controller and at least one electrode of the substrate, the electronic controller of the handheld body being configured to:
operate the pump to aspirate one or more fluids including said ion channel containing lipid cellular membrane into the fluid pathway and substrate of the pipette tip;
determine the electrophysiological properties of the cellular membrane ion channel, while the ion channel containing lipid cellular membrane makes contact with at least one of said electrodes of the substrate, and to simultaneously record current from one of said electrodes; and
output data representative of the recorded current.

16. A method for analysis of electrophysiological properties of a cellular membrane ion channel in an ion channel containing lipid cellular membrane, the method comprising the steps of:
providing a handheld body, the body comprising a housing including a pump and an electronic controller;
providing a disposable pipette tip separate from the body, the pipette tip comprising a pathway for fluid, said pathway connecting an open end of the pipette tip to an analysis substrate adapted to transmit an electrical current through the ion channel in said ion channel-containing lipid cellular membrane, when said lipid cellular membrane is held at a predetermined site of the substrate;

releasably attaching the pipette tip to the body with the open end of the pipette tip being exposed to an exterior environment, the pump of the handheld body hydraulically connected to said pathway, and the electronic controller electrically connected to at least one of said electrodes of the substrate;

operating the pump to aspirate one or more fluids including said ion channel containing lipid cellular membrane into the fluid pathway and substrate of the pipette tip;

determining the electrophysiological properties of the cellular membrane ion channel, while the ion channel containing lipid cellular membrane makes contact with at least one of said electrodes of the substrate, and while the electronic controller records current from one of said electrodes; and causing the controller to output data representative of the recorded current.

17. The method according to claim 16, wherein an opening at the open end of the pipette tip is larger than the lipid cellular membrane, so as to allow the lipid cellular membrane to be aspirated into the fluid pathway of the pipette tip.

* * * * *